United States Patent [19]

Seitzinger

[11] Patent Number: 5,362,294

[45] Date of Patent: Nov. 8, 1994

[54] SLING FOR POSITIONING INTERNAL ORGAN DURING LAPAROSCOPIC SURGERY AND METHOD OF USE

[76] Inventor: Michael R. Seitzinger, Rte. 7, Box 124, Santa Fe, N. Mex. 87505

[21] Appl. No.: 951,567

[22] Filed: Sep. 25, 1992

[51] Int. Cl.$^5$ ............ A61F 2/00; A61F 13/00
[52] U.S. Cl. ............ 600/37; 623/13; 606/231; 604/11
[58] Field of Search ............ 600/37; 606/127, 128, 606/151, 191, 228, 231, 197, 198; 602/4; 623/13; 604/11, 15

[56] References Cited

U.S. PATENT DOCUMENTS

| | | | |
|---|---|---|---|
| 3,125,095 | 3/1964 | Kaufman et al. | 606/231 |
| 3,875,928 | 4/1975 | Angelchik | 600/37 |
| 4,098,728 | 7/1978 | Rosenblatt | 521/141 |
| 4,217,890 | 8/1980 | Owens | 128/1 |
| 4,428,375 | 1/1984 | Ellman | 128/334 |
| 4,973,300 | 11/1990 | Wright | 600/37 |
| 4,979,956 | 12/1990 | Silvestrini | 623/13 |
| 5,074,867 | 12/1991 | Wilk | 606/128 |

FOREIGN PATENT DOCUMENTS

9201433  2/1992  WIPO ............ 604/11

OTHER PUBLICATIONS

A. Thom, et al., *Experience with High-dose Radiation Therapy and the Intestinal Sling Procedure in Patients with Rectal Carcinoma*, Cancer 581 (Aug. 1, 1992).

J. T. Soper, et al., *Absorbable Synthetic Mesh (910-polyglactin) Intestinal Sling to Reduce Radiation-induced Small Bowel Injury in Patients with Pelvic Malignancies*, Gynecological Oncology 283 (Mar. 1988).

*Primary Examiner*—Randall L. Green
*Assistant Examiner*—Paul Prebilic
*Attorney, Agent, or Firm*—Darby & Darby

[57] ABSTRACT

A sling is disclosed for retracting a body organ such as the uterus or bowel during a laparoscopic surgical operation. The sling is made of an appropriate material with suitable dimensions so that it can be inserted through a cannula customarily used for laparoscopic surgery. At each end of the sling a suture and surgical needle is provided. In use, the sling is pushed into the abdominal cavity, opened and one needle pushed through the patient's abdominal wall and clamped to anchor the sling. The sling is then positioned to support the body organ, and the second needle passed through the abdominal wall from inside the patient and clamped outside the patient to hold the body organ in the retracted position. After the operation, the sutures inside the body cavity are cut and the sling pulled through a cannula by means of suitable surgical grasping means.

4 Claims, 1 Drawing Sheet

SLING FOR POSITIONING INTERNAL ORGAN DURING LAPAROSCOPIC SURGERY AND METHOD OF USE

This invention relates to a sling for positioning or retracting an internal organ during laparoscopic surgery.

Laparoscopic operations involve operations within the peritoneal cavity by means of instruments introduced into the cavity through tubular members or cannulas inserted through the abdominal wall. In such operations, a gas such as carbon dioxide is commonly pumped into the peritoneal cavity to create a space in which the surgeon can work. The presence of gas within the peritoneal cavity is known as the pneumoperitoneum.

In laparoscopy, several perforations are made in the patient's abdominal wall by means of trocars after which tubular members or cannulas are positioned in the openings formed by the trocars to permit the surgeon to view the operating site and to enable the surgery within the abdominal cavity. Laparoscopy provides advantages over conventional incision based surgery in that the perforations are less traumatic and result in faster recovery with concomitant benefits in terms of comfort and expense. Moreover, laparoscopic surgery is usually less time consuming and less expensive than incision based surgery.

In various laparoscopic surgical procedures, in is desirable to position an internal organ so that it does not interfere with the surgical procedure. This is not only for the surgeon's convenience but also because of the desirability of avoiding damage to the organ. For example, in a typical gynecological operative laparoscopy, such as an oophorectomy (removal of the ovaries), it is very often necessary to manipulate or position the uterus while maintaining the pneumoperitoneum after a colpotomy has been made. Obviously, the uterus cannot be manipulated by instruments that would tend to penetrate or otherwise damage it. Likewise, in many cases, the patient's bowel may interfere with the surgery. Currently, retractors are used by the surgeon to move the bowel away from the surgical site. In some operations, the patient is placed in what is known as the Trendelenburg position, sometimes at steep angles, in order to keep the bowel out of the surgeon's way. In this position, the head is lowered causing increased blood flow to the brain which is generally undesirable.

Thus, there is a need for a device which can be used during laparoscopic surgery to retract a body organ such as the uterus or bowel without trauma to the organ while the patient rests in a normal operating position.

SUMMARY OF THE INVENTION

In accordance with the invention, a sling for retracting a body organ, such as the uterus or bowel, is made of a biologically inert material with dimensions small enough that the material can be passed through a conventional cannula of the type used in laparoscopic operations. The sling is large enough to support the body organ to be retracted when the sling is opened after it has been pushed through the cannula. A suture and needle are attached to each end of the sling.

After the sling is passed through the cannula, the surgeon pushes one of the needles through the abdominal wall and clamps the needle outside the patient. The sling is then positioned with respect to the body organ so that the organ can be retracted to the desired position and the other needle then passed through the abdominal wall and similarly clamped outside the patient to support the organ in the retracted position. When the operation is complete, the sutures are cut and the sling removed from the organ which returns to its normal position. The sling is next withdrawn through the cannula by means of a suitable grasping instrument.

IN THE DRAWINGS

DETAILED DESCRIPTION

As indicated above, the invention has utility with various different body organs which may need to be retracted during laparoscopic surgery. Typically, such body organs include the bowel, uterus, ovaries and fallopian tubes. The preferred embodiment was developed specifically to retract the uterus during gynecological laparoscopy and, accordingly, the invention is illustrated and described as a uterine sling.

Figure 1:
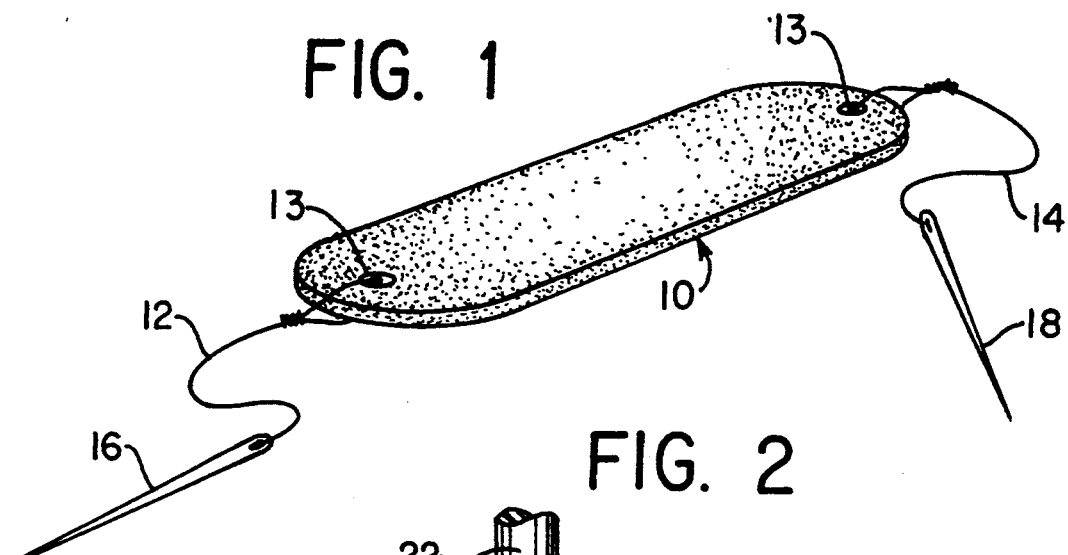
FIG. 1 illustrates a uterine sling in accordance with the preferred embodiment of the invention.

As shown in FIG. 1, a sling according to the invention comprises an elongated web 10 having lead sutures 12 and 14 connected at opposite ends and needles 16 and 18 attached to the sutures 12 and 14, respectively. Sutures 12 and 14 may be connected to the web 10 by means of grommets or rivets 13 to prevent tearing of the web material.

In the preferred embodiment, the web 10 is made of a biocompatible surgical sponge such as MEROCEL sponge sold by Merocel Corporation of Mystic, Connecticut. MEROCEL sponge is a polymeric, elastomeric lint-free, uniformly swellable, hydrophilic sponge having a uniform pore geometry and pore size distribution throughout its volume (see U.S. Pat. No. 4,098,728). The sponge when dry, can be packed into a small tube but expands when moistened to form a soft, flexible material capable of retracting a uterus or other body organ. By way of example, the web 10 may be approximately four inches long and one inch wide with a thickness of about ⅛ inch when dry. The preferred MEROCEL sponge material, when wet, expands to a thickness of about ¼ inch. The lead sutures may be six to eight centimeters in length and the needles four to five centimeters long and of the type commonly known as Keith needles.

Figure 2:
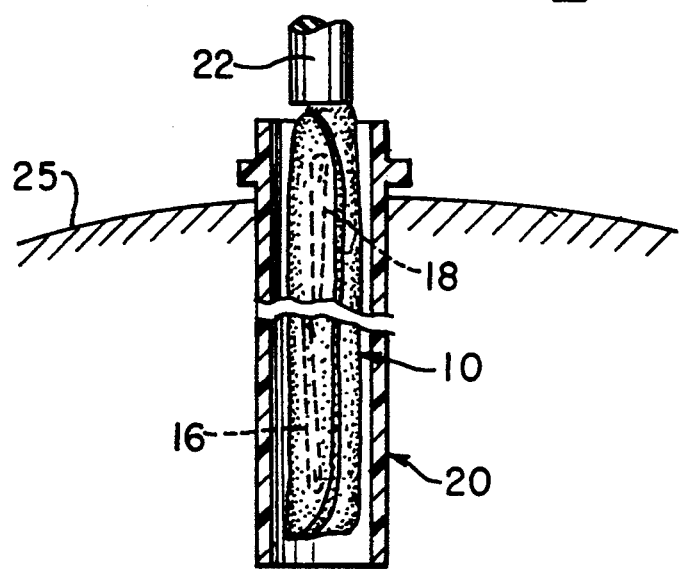
FIG. 2 shows the manner in which the sling may be forced through a cannula into the abdominal cavity.

As indicated above, the material and dimensions of the sling must be such that it can be inserted through a cannula commonly used in laparoscopic surgery. Typically, such cannulas have inner diameters of either five or ten millimeters. The material described above can be folded with the needles and sutures inside the material and readily inserted through a 10 mm port when dry. FIG. 2 shows a cannula 20 with a sling 10 wound to reduce its size within the cannula, the needles 16, 18 and sutures 12, 14 being retained inside the wound sling. A rod 22 is used to push the sling through the cannula 20 in the course of the operation when it is desired to retract the uterus.

Figure 3:
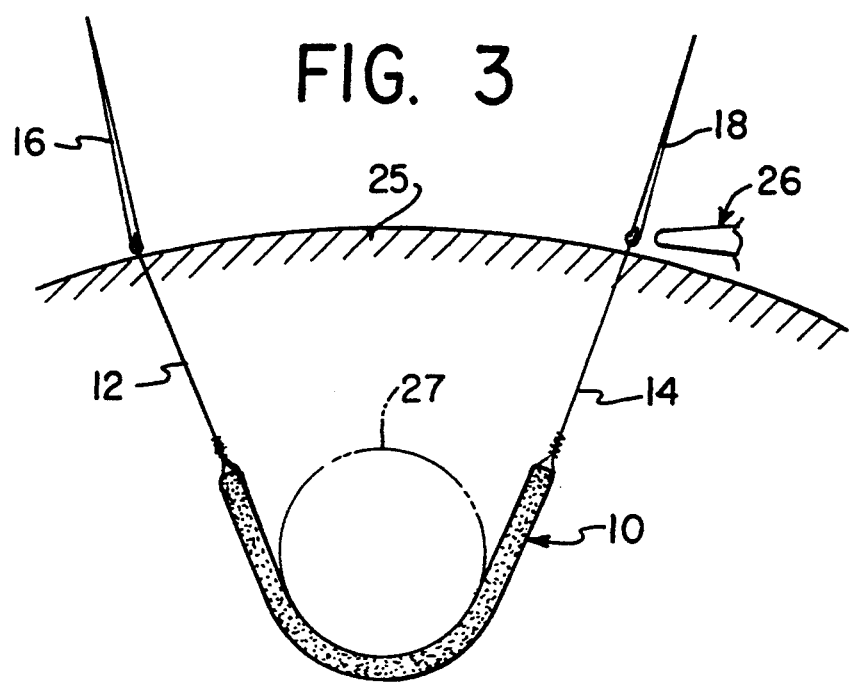
FIG. 3 is a schematic illustration showing how the sling is used to support a body organ during laparoscopic surgery.

In use, the wound sling is inserted into the abdominal cavity. The uterus is elevated from below and properly positioned. The sling material 10 is then moistened, for example, using a saline solution or water causing it to expand and open at least partially within the cavity. The surgeon then grasps one of the needles with a suitable grasping tool through one of the laparoscopic cannulas positioned in the abdominal wall and passes one of the needles 16 through the abdominal wall from inside until the needle exits from the patient. This is shown schematically in FIG. 3 in which the needle 16 extends from the patient's abdomen 25 where it can be grasped within an appropriate hemostat or clamp 26 and held in place.

With one end of the sling anchored, the surgeon then grasps the other end and passes it beneath the fundus 27 of the uterus and the second needle 18 is then passed through the abdominal wall and similarly grasped by a hemostat or clamp 26. The surgeon can retract the uterus to the desired position by pulling on one or both needles 16, 18 and clamping the needles in a desired position. The arrangement is such that the surgeon can easily change the position of the uterus during the surgical procedure.

When the operation is complete or when it is no longer necessary to retract the uterus, the lead sutures 12 and 14 are cut from inside the abdomen using conventional surgical tools inserted through the laparoscopic cannulas already in place. The needles and clamps are, of course, outside the patient. The surgeon then inserts a grasping instrument through the cannula and pulls the sling 10 through the cannula to remove it from the patient.

It is contemplated that the sling may be made in small, medium and large sizes depending, of course, on the size of the uterus. With the MEROCEL sponge material used in the preferred embodiment with the stated dimensions, the used sling can be easily removed through a 10 mm port.

I claim:

1. A sling for use in retracting a body organ within a body cavity, said sling being made of a biologically inert sponge material which expands when moistened and having dimensions such that it is capable of being passed through a cannula into the body cavity and of being expanded, for retracting the body organ, said sling further including lead sutures connected to opposite ends thereof and needles connected to the lead sutures, whereby said sling can be used to retract the body organ with the needles passing through the abdominal wall of the patient so that the body organ can be held in a desired position during a laparoscopic operation.

2. A method of retracting a body organ during laparoscopic surgery, comprising:
passing a sling through a canula into a body cavity of said body organ;
placing said sling in juxtaposition with said body organ; and
attaching said sling to the abdominal wall of the patient in a desired position to retract the body organ within said body cavity.

3. A method of retracting a body organ according to claim 2, wherein said sling includes needles attached thereto and wherein said sling is secured to the patient's abdominal wall by passing said needles through the abdominal wall from inside the abdominal cavity.

4. A method of retracting a body organ according to claim 3, wherein said needles are secured by clamping devices outside of the patient.

* * * * *